United States Patent [19]

Scheiner

[11] Patent Number: 5,527,822
[45] Date of Patent: Jun. 18, 1996

[54] METHOD OF TREATMENT OF TRAUMATIC BRAIN INJURY

[75] Inventor: Stuart L. Scheiner, East Brunswick, N.J.

[73] Assignee: Forest Laboratories, Inc., New York, N.Y.

[21] Appl. No.: 174,829

[22] Filed: Dec. 29, 1993

[51] Int. Cl.$^6$ .......................... A61K 31/36; C07D 443/00
[52] U.S. Cl. ............................................. 514/465; 549/306
[58] Field of Search ............................ 549/306; 514/465, 514/410

[56] References Cited

U.S. PATENT DOCUMENTS

| 4,518,611 | 5/1985 | Veltri | 514/470 |
|---|---|---|---|
| 4,620,014 | 10/1986 | Szent-Gyorgyi et al. | 548/545 |
| 4,883,808 | 11/1989 | Fodor et al. | 514/468 |
| 4,883,813 | 11/1989 | Maxim et al. | 514/470 |
| 5,098,933 | 3/1992 | Veltri et al. | 514/470 |
| 5,102,909 | 4/1992 | Veltri et al. | 514/470 |

OTHER PUBLICATIONS

The Congress Of Neurological Surgeons, 43RD Annual Meeting, Vancouver, Canada, Oct. 2–7, 1993, pp. 70–71.

*Primary Examiner*—Shean C. Wu
*Attorney, Agent, or Firm*—Graham & James

[57] ABSTRACT

A method of treatment of a mammal, including humans, suffering from traumatic brain injury, which comprises administering to the sufferer a therapeutically effective amount of a butyrolactone derivative.

12 Claims, 13 Drawing Sheets

METHOD OF TREATMENT OF TRAUMATIC BRAIN INJURY

The present invention is directed to a method of treatment of traumatic brain injuries.

It is widely accepted that severe traumatic brain injuries (TBI) initiate a cascade of events that lead to dramatic elevation of intracranial pressure (ICP) and dysfunction of cerebrovascular regulatory mechanisms essential for survival. Indeed, ischemic brain injury is seen universally in those patients who die following severe TBI. Intracranial hypertension (IH) following traumatic brain injury is associated with direct effects on cerebral perfusion which may be responsible for secondary ischemia. The contributions of both post-traumatic cerebral edema and alteration in cerebral blood volume to ICP appear to vary based on the length of time after the primary mechanical insult. This combination of vasomotor dysfunction and abnormalities in vascular permeability is characteristic of acute inflammation.

The present invention now provides a method of treatment of traumatic brain injuries in mammals, including humans, by administering to a mammal suffering from traumatic brain injury a therapeutically effective amount of a butyrolactone derivative of the formula

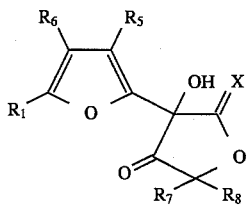

(I)

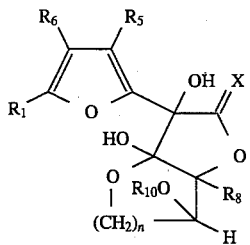

(II)

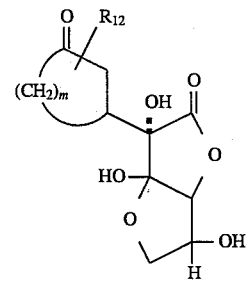

(III)

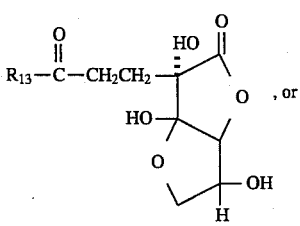

(IV) , or

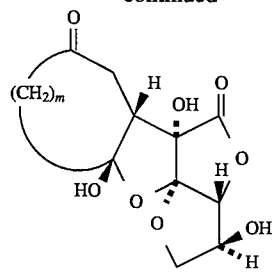

(V)

wherein:

$R_1$ is selected from the group consisting of hydrogen and lower alkyl;

$R_2$ is selected from the group consisting of hydrogen, lower alkyl and $CH_3YCH_2-$;

$R_5$ and $R_6$ are selected from the group consisting of hydrogen and lower alkyl and may be the same or different;

$R_8$ is selected from the group consisting of hydrogen and lower alkyl;

$R_7$ may be $R_8$ or

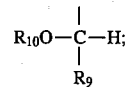

$R_9$ is selected from the group consisting of

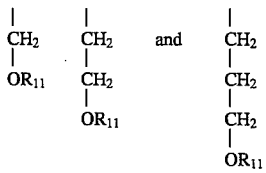

$R_{10}$ and $R_{11}$ are selected from the group consisting of hydrogen, lower alkyl, phenyl and hydroxyl substituted lower alkyl and may be the same or different;

when $R_7$ contains a hydroxyl group in the $\alpha$, $\beta$ or $\gamma$ position, $R_7$ may form the hemiketal ring closure at carbon 3 of the butyrolactone with protonation of the carbonyl group on the same carbon atom;

$R_{12}$ is selected from the group consisting of hydrogen, lower alkyl and lower haloalkyl;

$R_{13}$ is lower alkyl;

m is 2, 3 or 4;

n is 1, 2 or 3;

X is O, S or NH; and

Y is O or S.

Compounds of formulas (I) to (V) are known and have been proposed for use for various therapeutic indications. U.S. Pat. Nos. 4,518,611, 4,620,014, 4,833,808, 4,883,813, 5,098,933 and 5,102,909, which are incorporated herein by reference thereto, describe these compounds, methods for their preparation and methods for formulating these compounds into pharmaceutical compositions.

U.S. Pat. No. 4,883,813 proposes the use of certain butyrolactone derivatives for treatment of inflammation in mammals, such as acute inflammation. However, none of the prior art has proposed the use of compounds (I) to (V) for the treatment of traumatic brain injury. As is known, the treatment of traumatic brain injury with steroidal or non-steroidal anti-inflammatory drugs is not likely to be successful due to a number of factors, including the inability of conventional anti-inflammatory agents to cross the blood-brain barrier. It was therefor unexpected that the butyrolactone derivatives used in the present invention would be useful in the treatment of traumatic brain injury.

It is presently preferred to use the following compounds in the treatment of traumatic brain injury according to the present invention:

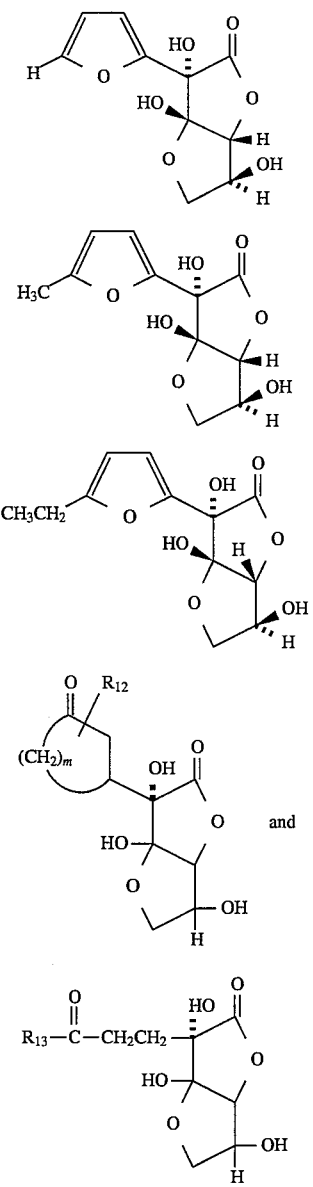

wherein $R_{12}$ is lower alkyl, m is 2, 3 or 4, and $R_{13}$ is hydrogen, lower alkyl or lower haloalkyl, and Y is O or S.

It is most preferred at present to use the compound referred to as Methoxatone, which has the formula

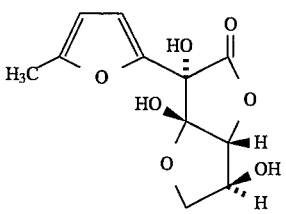

It is presently believed that compounds (I) to (V) exert their attenuating effect on post-traumatic intracranial hypertension by reducing both the cerebrovascular permeability defects that promote edema formation, as well as blunting the, as yet, undefined stimulus for inflammatory cell infiltration. It is believed that the biochemical foundation for the clinical manifestations of TBI, namely cerebrovascular permeability and vasomotor dysfunction, lies in the generation of inflammatory mediators by resident cells of the central nervous system and/or infiltrating leukocytes. Based on the current understanding of the pathophysiology of TBI, the anti-inflammatory effects of compounds (I) to (V) would be therapeutically beneficial in the treatment of severe head injury.

It is presently preferred to administer compounds (I) to (V) parenterally, such as intravenously, in a bolus, so as to obtain the most rapid delivery of the active agent to the brain. A suitable daily dosage for obtaining attenuation of the effects of traumatic brain injury is from about 10 to about 1000 mg/kg body weight, although the optimum dosage of the compound (I) to (V) will be determined by the physician taking into account the age, weight and general health of the subject. The daily dosage may also be administered in one or several treatments over a period of time, such as by way of single or multiple doses per day or from sustained release compositions.

The compounds (I) to (V) may be administered alone or, more usually, in the form of a pharmaceutical composition comprising a therapeutically effective amount of the active agent in combination with an inert pharmaceutically acceptable diluent or carrier therefor. The choice of the diluent or carrier will be determined by the route of administration, the solubility of the compound and standard pharmaceutical practice.

Oral and parenteral dosage units will be prepared in accordance with standard procedures and may contain the selected active compound (I)–(V) as the only or principal active ingredient in the composition. Any of a wide variety of known inert excipients may be employed to prepare useful compositions. These include, for example, dextrose, starch, talc, various types of clay, mineral oil, cottonseed or sesame oil, as well as water or various miscible and immiscible aqueous compositions in which the therapeutic agent is soluble or may be suspended with the aid of known surfactants.

For buccal and sublingual administration, the active ingredient can be formulated in tablet form with water-soluble binding agents, such as lactose or other palatable carbohydrates.

For rectal administration, suppositories or inserts containing the active ingredient dispersed in such reagents as cocoa butter, petrolatum, or other natural lubricants or in a synthetic emollient such as polyethylene glycol 1000 or polyethylene glycol 4000 may be used.

It may be convenient to administer Compounds (I) to (V) from sustained release dosage forms. A number of compositions suitable for such preparations are known and can be usefully employed. For oral, sustained release administration, the selected therapeutic agent may be in a time disintegrating tablet or pellet coated with various thicknesses of known materials such as carnauba wax, cellulose esters and ethers, fats, keratin, gluten or various natural or synthetic esters. Tablets in which the selected agent is contained in a slowly dissolving core such as dehydrogenated castor oil or fatty acids can also be employed. Alternatively, the active material can be bound to an ion exchange resin such as a sulfuric acid type cation exchange resin.

A number of transdermal formulations are possible for use in the practice of this invention. They are discrete dosage forms in construction systems which, when applied to the skin, deliver the therapeutic agent through the skin at a controlled rate for systemic circulation. A transdermal device typically comprises an outer covering barrier, a drug reservoir which may have a rate of release controlling membrane, a contact adhesive applied to some or parts of the device at the device/skin interface and a protective layer which is removed before applying the device. The drug reservoir is normally some type of polymer matrix such as a polyvinylpyrrolidone or a silicone polymer from which the drug is slowly released. A microporous membrane such as a polypropylene film may serve as a membrane to control the rate of release.

The compounds (I)–(V) may also be used in association with other therapeutic agents including, for example, antibiotics or antiviral agents.

Figure 1A:
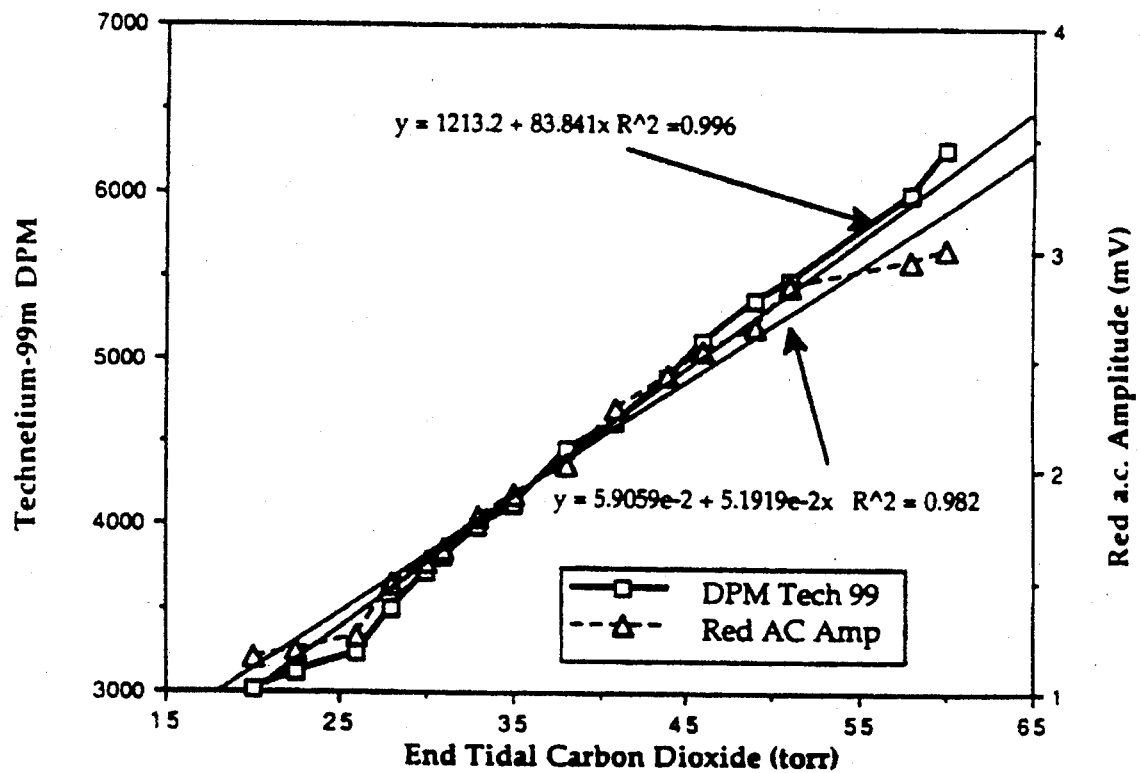
FIGS. 1A and 1B present data used to calculate cerebral blood volume.
Figure 1B:
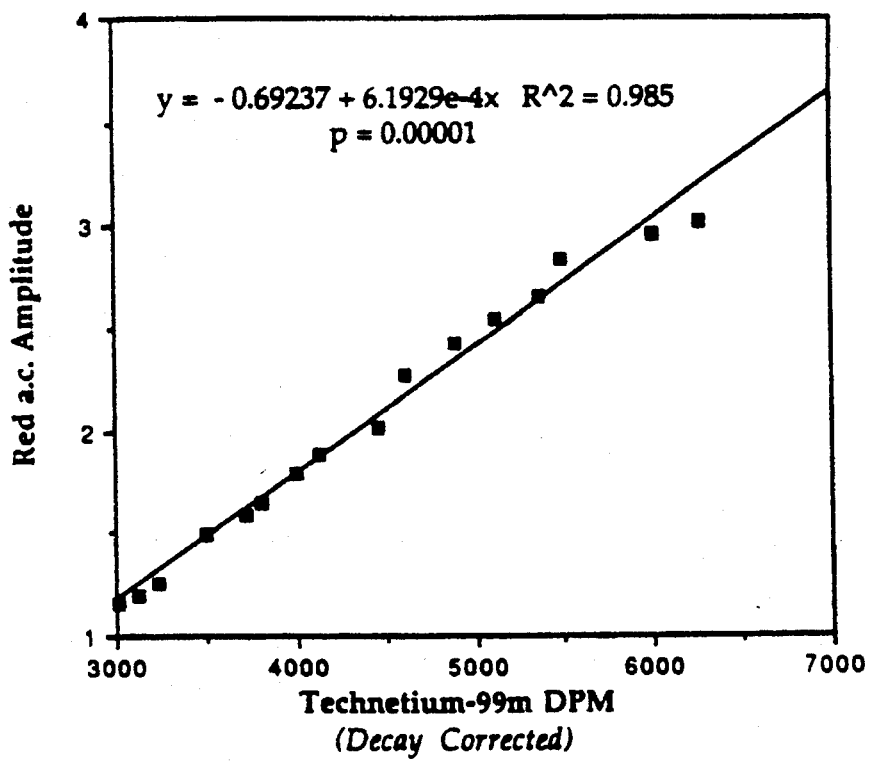

The following Example illustrates the present invention through the use of an accepted animal model for traumatic brain injury. This Example refers to FIGS. 1–5 of the accompanying drawings, and to Tables I–III, which follow the Example.

EXAMPLE

Twenty female miniature Yucatan swine (Charles River Laboratories) were employed in this study. Experiments were conducted in accordance with the Animal Welfare Act and approved by the Institutional Animal Care and Use Committee of Cornell University Medical College. The animals were premedicated with ketamine and xylazine, weighed, and brought to the surgical laboratory where anesthesia was induced with isoflurane by mask. They were then intubated, placed supine, and ventilated with an anesthetic gas mixture (oxygen 23%, nitrogen 75%, isoflurane 2%) to maintain normal arterial blood gases. The left femoral artery and vein were cannulated for continuous arterial blood pressure monitoring and placement of a flow-directed pulmonary artery catheter for central venous pressure (CVP), pulomary artery (PA) and pulmonary capillary wedge pressure (PCWP) monitoring. A cystotomy was performed and a 14 French Foley catheter was placed for urine output monitoring. The right subclavian vein was cannulated for venous access. A rectal thermistor was placed for core temperature monitoring. The animals were then repositioned prone and the heads were immobilized in a frame. The skull was exposed though a sagittal scalp incision and both cerebral ventricles were cannulated using the right-angle technique. Intracranial pressure was continuously monitored with a fiberoptic pressure transducer (Camino Labs, San Diego, Calif.). An 18-gauge teflon catheter placed in the contralateral ventricle confirmed ICP by manometry. The sagittal sinus was catheterized with a PE-10 polyethylene cannula for sagittal sinus pressure (SSP) monitoring. A 14-mm burr hole was made through the right frontal bone, with care taken to avoid injury to the underlying dura. A hollow stainless steel tube (injury screw), 14 mm in outer diameter and threaded at one end, was screwed into the burr hole. The injury screw was cemented in place to form a water-tight seal with methylmethacrylate, and attached to a fluid percussion device by a 3-cm length of nondistensible Tygon® tubing. The system was filled with normal saline at 37° C. and purged of air.

Animals were maintained normothermic with a heating lamp, and euvolemic with the intravenous infusion of Ringer's lactate to maintain CVP between 2 and 5 mm Hg and urine output $\geq 0.5$ ml/kg/hour during the baseline period. Animals were allowed to equilibrate for a 30-minute period prior to experimental injury. The following physiological variables were continuously monitored using an analog-to-digital conversion data acquisition system: mean arterial blood pressure (mABP), CVP, PA, PCWP, SSP, ICP, heart rate (HR), inspired ($FiO_2$) and expired ($FeO_2$) oxygen concentrations, expired isoflurane concentration, end tidal $CO_2$ ($PetCO_2$), and core temperature. Arterial blood gas determinations were made at 30 minute intervals in 300 μl samples (Blood gas analyzer Model 288, Ciba Corning, Medfield, Mass.).

Determination of Brain Compliance

Brain compliance was determined using the single injection method decribed by Marmarou, et al. For each of the determinations, made at least 5 minutes apart, a 0.5 mL bolus infusion of normal saline, maintained at 37° C., was given over 0.5 seconds. The ICP immediately prior to injection was defined as $P_o$, and the highest pressure recorded after injection was defined as $P_{max}$. The pressure-volume index (PVI) was calculated using the following equation:

$$PVI = V/\text{Log } P_o/P_{max}$$

where V=volume of the bolus infused. Once the PVI was calculated, brain compliance was derived from the equation:

$$\text{Compliance} = 0.4343 \text{ PVI}/P$$

where P is the ICP at the point when the compliance measurement was determined and 0.4343 is a constant. A minimum of three determinations were made during the baseline period in all animals.

Fluid Percussion Injury

Experimental traumatic brain injury was induced by fluid percussion injury, modified from the method described by Sullivan. A 2.5 Atm barotraumatic injury was delivered to the brain over 20 to 25 milliseconds through the right frontal injury screw. Pressure was measured at the distal end of the fluid percussion piston by a high resolution transducer (Statham, Puerto Rey, Puerto Rico) Following percussion, the injury screw was disconnected from the fluid percussion device, the screw removed from the skull, and the cranial detect covered with bone wax to maintain the injured area as close to core temperature as possible. Previous work has demonstrated that this degree of barotrauma resulted in a reproducible injury characterized by histopathological evidence of a severe frontal lobe injury, including development of frontal contusion and intracranial hypertension, without brain stem deformation that could affect cardiopulmonary performance.

Animals were divided into three groups. Group I (n=6) was subjected to TBI, Group II (n=6) was subjected to TBI and received an i.v. bolus injection of methoxatone ("METH") 100 mg/kg, one hour following injury, Group III (n=8) was a surgical sham.

Preparation of Drug

Crystalline, lyophilized methoxatone was maintained at −20 C until it was reconstituted in phosphate buffered saline to a concentration of 100 mg/ml immediately prior to each experiment. Methoxatone at a dose of 100 mg/kg body weight was delivered via intravenous bolus injection 60 minutes following injury. Serum samples were obtained at various time points following administration of the compound for the determination of serum concentration by High Pressure Liquid Chromatography (HPLC).

Determination of Cerebral Blood Volume

Since cerebral blood flow and volume increase linearly with PaCO2 (Hampton et al), the rate of respiration was manipulated to produce varying $PaCO_2$ ($PetCO_2$) in order to determine the changes in CBV as measured by cerebral cortical reflectance photoplethysmography and Technetium-99 m labeled red blood cells

Cerebral Cortical Reflectance Photoplethysmography

A 14 mm burr hole was made in the frontal region, contralateral to the injury screw, in all animals for epidural placement of a flexible reflectance photoplethysmography probe. The probe consisted of miniature red and infrared light-emitting diodes (LED's) and a silicon photodetecting diode mounted on a flexible circuit board. Output from the photodetector was selectively tuned to provide data on photostimulation by specific wavelengths. The probe was connected to a photodemodulation circuit and an analog-to-digital converter connected to a microcomputer (Macintosh II, Apple Computer, Cupertino, Calif.), Reflected red and infrared photoplethysmograms were employed to evaluate cerebral cortical blood volume and oxygen saturation of hemoglobin ($SaO_2$), Amplitudes of the reflected signals were used in the calculation of $SaO_2$ (oximetry) and as an index of cerebral blood volume.

Hemoglobin within cerebral cortex, illuminated by the LED's on the surface of the probe, reflects red and infrared light which is detected by the photodiode. The intensity of the red and infrared signals varies with the cardiac cycle and is dependent upon the $SaO_2$. The oximetry technique analyzes the pulsatile (referred to as the a.c. component), rather than absolute, non-pulsatile (referred to as the d.c. component), reflected light intensity of red and infrared photoplethysmograms, measured at 660 and 910 nm, respectively. The wavelengths chosen represent portions of the spectral region where the absorption coefficients of reduced and oxygenated hemoglobin in tissue are markedly different (660 nm), and where they are relatively similar (910 nm). An isobestic wavelength (820 nm), where the absorption coefficients for both oxygenated and reduced hemoglobin are roughly the same, was used as a reference for calibration. When the reflected d.c. signal remains constant, the amplitude of the reflected a.c. signal varies as a function of total hemoglobin within the illuminated tissue using algorithms previously employed in near-infrared spectrophotometry by Wyatt, et al. The sensitivity of this system to changes in cerebral perfusion in response to hypo- and hypercarbia was previously documented.

Prior to each experiment, correlation of calculated cerebral cortical arterial hemoglobin saturation to $SaO_2$ was established.

Technetium-99m ($^{99m}Tc$) Labeled Red Blood Cells

Cerebral blood volume (CBV) changes were simultaneously measured in some animals using radioactively labeled red blood cells (RBCs) to calibrate the reflectance photoplethysmographic technique. Briefly, 10 mL of whole blood was labeled with $^{99m}Tc$ using the modified in vivo method of Callahan, et al. This technique assures rapid (>90% efficiency within 5 minutes) and reproducible labeling. The labeled RBC's were then reinfused and regional CBV was measured directly by a gamma collimator placed over the site of the reflectance photoplethysmographic probe (FIG. 1). The collimator employed a 20 percent window over the 140-keV photopeak of $^{99m}Tc$. Arterial blood samples (2.0 mL), obtained at the time of gamma emmission data collection, were divided into three equal aliquots. One aliquot was used for the determination of total hemoglobin by co-oximetry (blood gas analyzer Model 288, Ciba Corning, Medfield, Mass.); the hematocrit was determined by microcentrifugation. The two remaining aliquots were placed in a well counter and total blood sample counts were decay corrected to the time they were drawn by the equation:

$$C_o = Ce^{\lambda t}$$

where $C_o$=decay-corrected counts, Ce=decayed counts, $\lambda$=0.693/6.02 hr physical half life of $^{99m}Tc$, and t=the time between when the sample was drawn and when it was counted. These data were then employed to calculate CBV, expressed as mL/100 g tissue, from the total counts obtained from the collimators.

Histological Analysis of Cerebral Cortex

Immediately following sacrifice, the supratentorial brain was removed intact and representative sections from the right frontal lobe directly under the injury screw, the left frontal lobe, the left occipital lobe and left parietal lobe were sharply dissected free and placed in neutral buffered formalin. The tissue was fixed for a minimum of 96 hours and then processed for light microscopy. Sections were then evaluated under blinded conditions, and graded according to the following convention:

Cerebrovascular Injury Index

Grade 0 Normal brain, no evidence of cerebrovascular inflammation, no intraparenchymal PMN's, no evidence of PMN margination or diapedesis Grade 1 PMN margination, minimal extravasation of RBC's, normal endothelium Grade 2 Extensive PMN margination with evidence of diapedesis of PMN's, with normal or swollen endothelium Grade 3 Extensive PMN Margination with diapedesis and intraparenchymal PMN's±extravastion of RBC's, swollen endothelium Grade 4 Extensive PMN Margination with diapedesis and intraparenchymal PMN's±extravastion of RBC's, with evidence of PMN phagocytosis of neurons and/or glia, gross disruption of endothelium and/or vascular basement membrane

Brain Specific Gravity Determination

Representative sections of brain tissue from identical regions employed for histological analysis were immediately placed in sealable polyethylene pouches and kept on ice until delivered to the laboratory for determination of tissue specific gravity. Three 1 mm cubes of tissue were sharply dissected from each specimen and placed in a kerosene/bromobenzene density gradient column and allowed to equilibrate. The column was calibrated against beads of known density. Measurements were taken after 2, 3, 5 and 10 minutes on the column to factor out non-specific evaporation of surface water in different specimens.

Data Analysis

Physiological data are expressed as mean±standard error of the mean. Differences between groups at each time point were compared using the Wilcoxon nonparametric analysis. A two-way analysis of variance (ANOVA) was employed to examine differences in individual variables within groups with respect to time. Correlation of individual physiological variables between multiple groups was evaluated using the Spearman ranked correlation coefficient. Histological data was compared using a two-sample t-test assuming unequal variances. A significance level of $p<0.05$ was used throughout this study.

RESULTS

Calibration of Photoplethysmographic Method of Determining CBV

To evaluate the accuracy of the photoplethysmographic technique for determing CBV changes in real time, simultaneous determinations were made by counting radioactively labeled RBC's in the same tissue region. Both $^{99m}Tc$ decay from labeled RBC's and the red a.c. amplitude derived from reflectance photoplethysmography were well correlated with changes in CBV that occured in response to variations in PET $CO_2$ (FIG. 1a). This relationship was significant ($p=0.00001$) throughout the range of photodetector sensitivity of the system (FIG. 1b), and when counts were corrected for decay. Total counts were then converted to a blood volume measurement based on the results of direct counting of whole blood specimens drawn during the experiment. From this relationship, calculation of CBV was made from the red a.c. amplitude alone.

Figure 2:
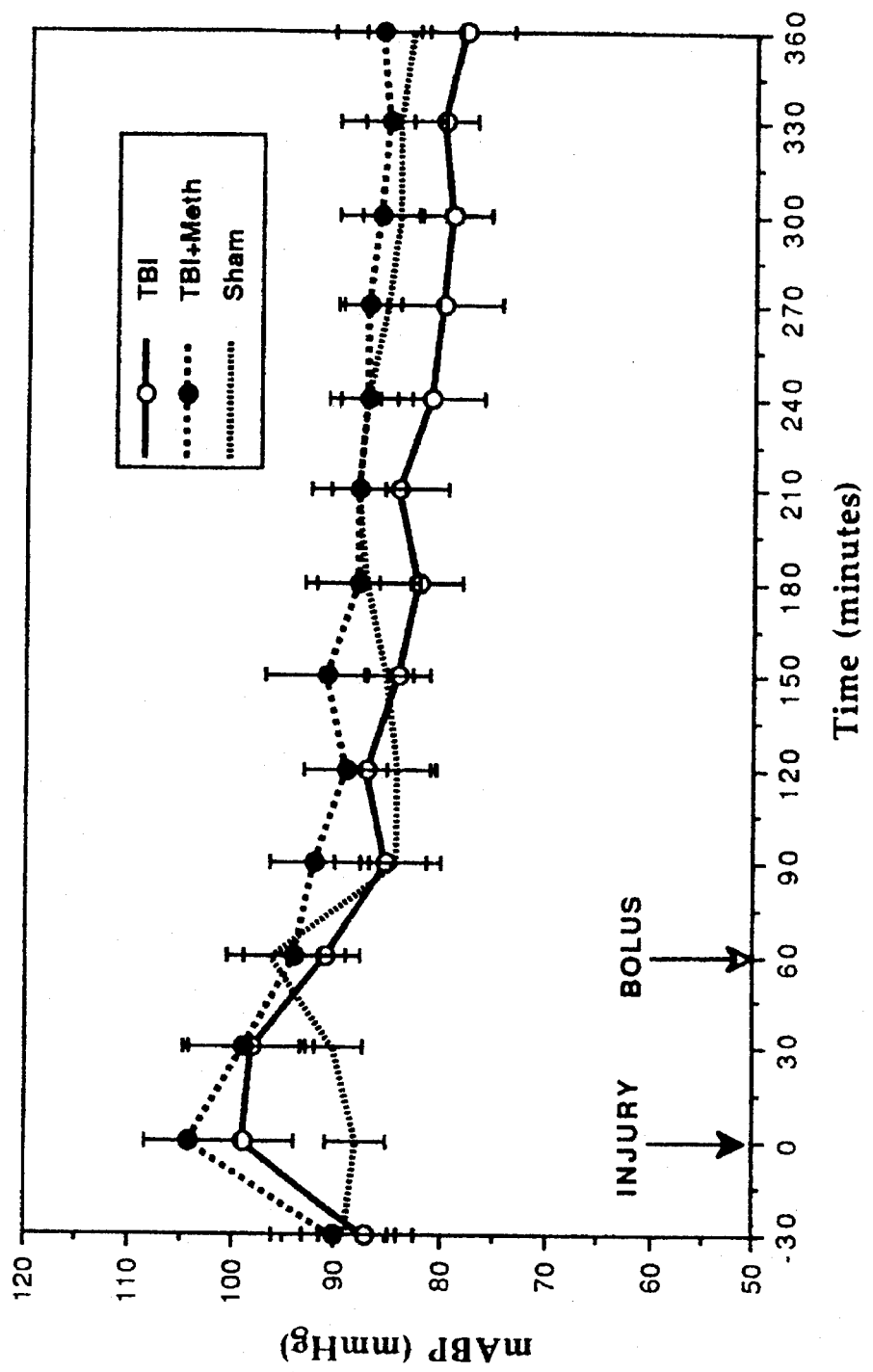
FIG. 2 shows transient systemic hypertension following traumatic brain injury.

Physiologic data, obtained 30 minutes following surgical preparation, demonstrated no statistically significant differences in baseline ICP, mABP, CVP, PCWP, and SVR between groups, Arterial blood gases and temperature were unchanged from baseline values throughout the duration of the experiment in all groups. Animals subjected to fluid percussion injury developed a significant, transient systemic hypertension following TBI that lasted approximately 30 minutes and then returned to baseline values (FIG. 2). Arterial blood pressure slowly decreased during the 6 hour experimental period in all animals, however, these changes in mABP were not statistically different when values were compared in head injured and sham treated animals.

Dramatic intracranial hypertension occurred immediately following TBI in injured animals (FIG. 3), rising to significantly higher levels from baseline (Group I; 22±3 vs 8±3, $p<0.001$ and Group II; 21±3 vs 9±2, $p<0.001$) within minutes of injury, and returning to near baseline levels within 60 minutes. ICP continuously rose in Group I during the subsequent 5 hours, and at 6 hours was significantly higher than baseline values (27±3 vs 8±3, $p<0.001$) as well as compared to sham (27±3 vs 7±2, $p<0.001$). In contrast, animals treated with Methoxatone showed a significant attenuation of this increase in ICP especially between 210 and 360 minutes post injury (FIG. 3), and at 6 hours was significantly lower than Group I (14±3 vs 27±3, $p<0.05$) In addition, the immediate post-injury rise in ICP that occurred during the period of systemic arterial hypertension was accompanied by an increase in CBV to more than double the baseline values in Groups I and II (19.2±1.4 vs 8.9±1.1 mL/100 g tissue, $p<0.05$) at the time of the greatest rise in ICP. Although CBV decreased from this peak at the time of injury, it remained significantly elevated above baseline levels throughout the experimental period in Group I. CBV returned to near baseline values in Group II by 60 minutes and remained at this level throughout the experimental period.

Arterio-venous oxygen content differences across the brain significantly decreased (1.9±0.1 vs 3.8±0.3 mL/dL, $p<0.05$) during the immediate post-traumatic rise in ICP and CBV, and was inversely related to the photoplethysmographically calculated cerebral cortical $SaO_2$. Oxygen extraction then gradually increased during the post-traumatic period and was significantly higher than baseline values from 3 to 6 hours following injury in Group I. In addition, calculated cerebral cortical $SaO_2$ initially rose after injury and then gradually declined to significantly lower than baseline values after 4 hours. Oxygen extraction was closer to baseline values in the 3 to 6 hour post-injury period in Group II.

Figure 4:
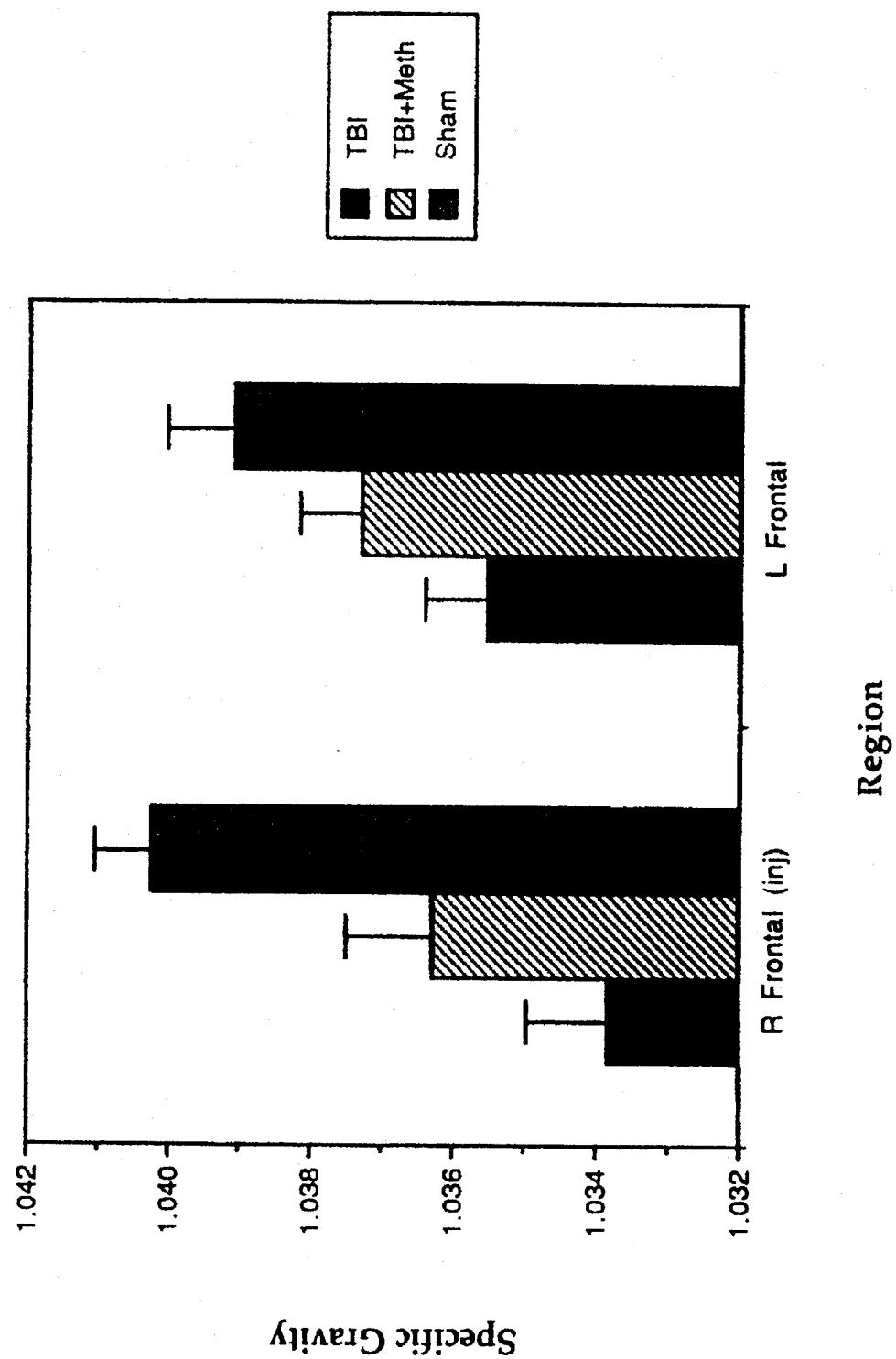
FIG. 4 shows brain water content in injured animals.
Figure 5A:
FIGS. 5A–5I are photomicrographs showing histological analyses of the lobes of injured animals.
Figure 5B:
Figure 5C:
Figure 5D:
Figure 5E:
Figure 5F:
Figure 5G:
Figure 5H:
Figure 5I:
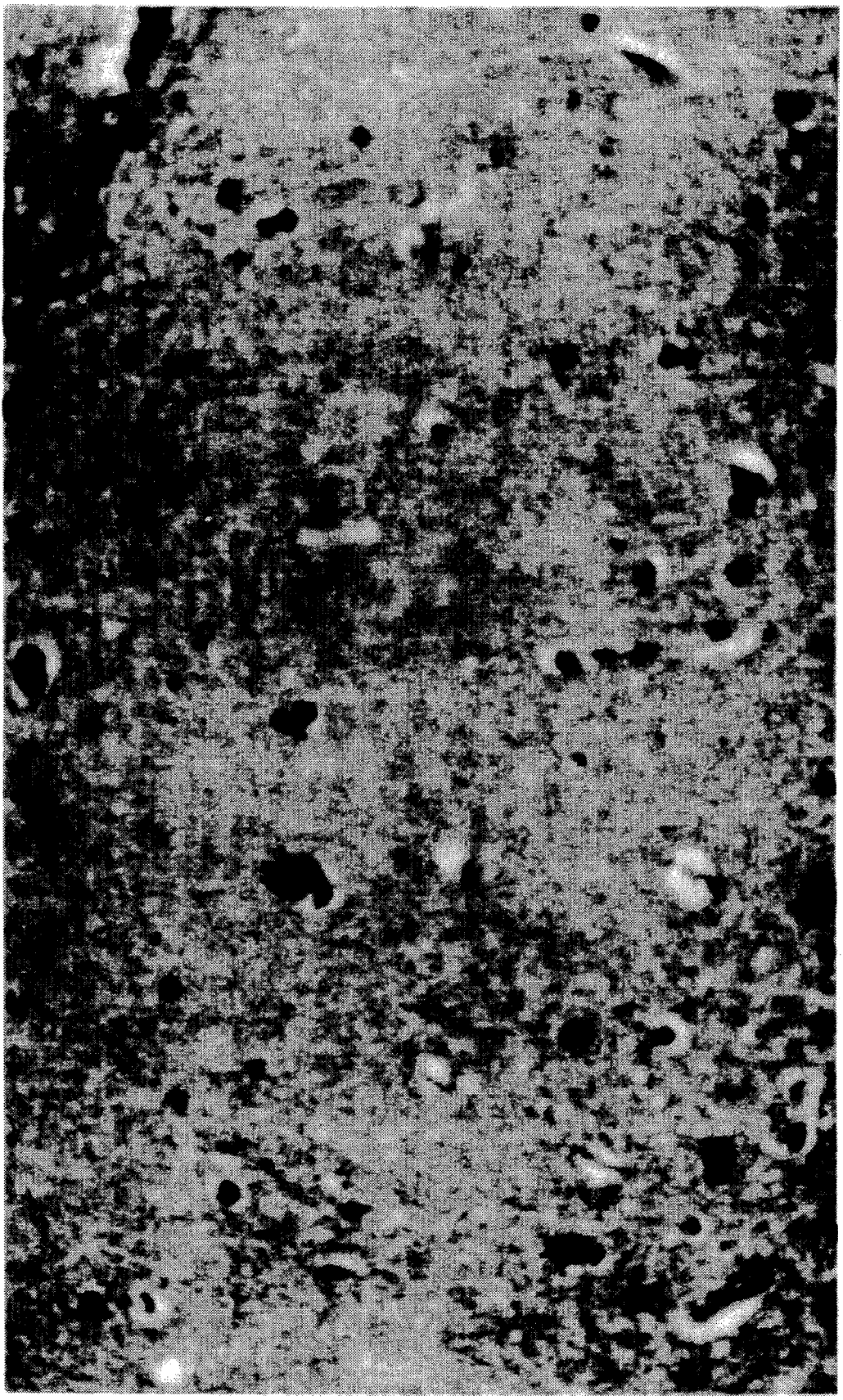

Brain water content determined by gravimetry was significantly higher in both the directly injured right frontal lobe and the adjacent left frontal lobe of animals in Group I compared to Group III controls (FIG. 4, Table 1). (Lower specific gravities correlate well with increased brain edema due to injury.) However, tissue water content of the injured right frontal lobe of animals treated with the Methoxatone was lower than untreated animals and approached statistical significance ($p=0.061$). The brain water content of the adjacent frontal lobe of treated animals was not statistically different from that present in the sham controls.

Histological analysis of the right and left frontal lobes of untreated, injured animals demonstrated evidence of cerebrovascular injury and inflammatory cell infiltration according to the grading scale described above. Based on the cerebrovascular injury index (CVII), the injured right and left frontal lobes in untreated animals showed significantly greater evidence of injury and inflammation than in the control group (Group III) (Table 2, FIG. 5 A–I). In contrast, the right frontal lobe in Methoxatone treated animals showed significantly less evidence of injury (CVII=1.7±0.5 vs 3.2±0.6, $p<0.05$), while the left frontal lobe in Group II was indistinguishable from uninjured controls.

SUMMARY

Figure 3:
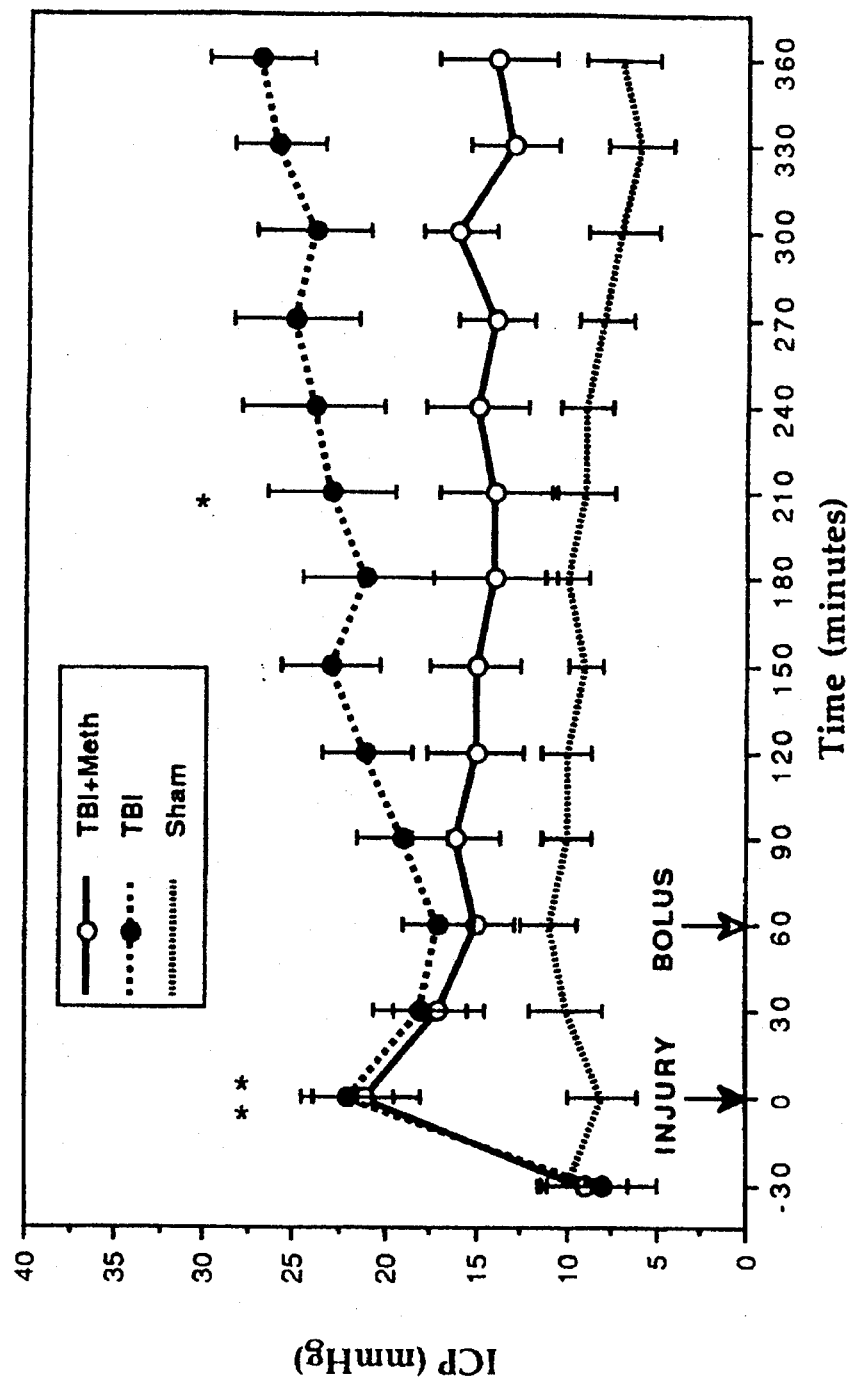
FIG. 3 shows intercranial pressure immediately following traumatic brain injury.

The pathophysiologic events that follow experimental TBI are well described. The development of intracranial hypertension, alterations in CBV and increase in brain tissue water content, increased oxygen extraction and histologic evidence of cerebrovascular injury and inflammation are characteristic of acute severe mechanical brain injury in this model. Methoxatone significantly attenuated the intracranial hypertension seen in untreated animals following TBI. Methoxatone appeared to exert its effect within 60 minutes of administration. As seen in FIG. 3, ICP remained significantly lower in the Methoxatone treated group compared to untreated controls, from 150 minutes following administration to the end of the experimental period. Although ICP was still significantly elevated in treated animals compared to sham controls, Methoxatone appears to protect the injured brain from the uncoupling of metabolic demand and cerebral blood flow as evidenced by the preservation of near-baseline oxygen extraction, compared to significantly elevated oxygen extraction in untreated animals.

Methoxatone treated animals developed less tissue edemas as measured by tissue specific gravity, approaching statistical significance (p=0.061) compared to untreated injured animals. This data suggests that Methoxatone reduces the post-traumatic defect in cerebrovascular permeability which promotes the movement of water into the tissue contributing to cerebral edema.

Methoxatone had a significant effect on post-traumatic inflammation, as evidenced by the lower CVII Histopathology scores in treated animals compared to untreated controls. Morphological evidence of cerebrovascular injury, namely infiltration of inflammatory cells, neutrophil margination and diapedesis, and neutrophil phagocytosis of pyknotic neurons was markedly reduced in treated animals.

TABLE 1

| Region | Group I TBI | Group II TBI + METH | Group III Sham |
| --- | --- | --- | --- |
| Right Frontal (Injury) | 1.033828 ± 0.00114 | 1.036264 ± 0.00122 | 1.040233 ± 0.00080 |
| Left Frontal (adjacent) | 1.035506 ± 0.00089 | 1.037278 ± 0.00089 | 1.039088 ± 0.00096 |

TABLE 2

Results: Cerebrovascular Injury Index

| Group | R Frontal (inj) | L Frontal (adjacent) |
| --- | --- | --- |
| TBI | 3.2 ± 0.6 | 1.3 ± 0.7 |
| TBI + Meth | 1.7 ± 0.5* | 0.5 ± 0.3** |
| Sham | 0.5 ± 0.2 | 0.6 ± 0.2 |

*$p < 0.05$
**$p < 0.01$

TABLE 3

Photomicrographs A-I of FIG. 5

A-(63 ×) Right frontal lobe section, sub-meningeal cortex, taken 6 hours following intracerebroventricular infusion of 20 uM LTC4. An intense meningovasculitis, characterized by margination and diapedesis of neutrophils, infiltration of neutrophils into the parenchyma, and meningitis with a dense neutrophil-rich exudate in the subarachnoid space.
B-(250 ×) Higher magnification from the section in A. Intraparenchymal neutrophils are shown phagocytizing an astrocyte. Multiple neutrophils are seen throughout the neuropil.
C-(160 ×) Right frontal lobe section, sub-meningeal cortex, taken 6 hours following intracerebroventricular infusion of 20 uM LTC4. Free intraparenchymal neutrophils (→A) Phagocytosis of pyknotic neurons by intraparenchymal neutrophils (→B)
D-(160 ×) Right frontal lobe section, sub-meningeal cortex, taken 6 hours following experimental TBI. Neutrophils are seen diapedesing through an apparently intact parenchymal vessel. Note the contraction artifact halo around the vessel indicating pre-fixation perivascular edema.
E-(160 ×) Right frontal lobe cortical section, taken 6 hours following experimental TBI. Free intraparenchymal neutrophils seen (→A). Neutrophil with intracellular inclusions representing phagocytized debris (→B).
F-(250 ×) Right frontal lobe cortical section, taken 6 hours following experimental TBI in animals treated with METH. Intraparenchymal arteriole without evidence of neutrophil margination. Numerous pyknotic cells without intraparenchymal neutrophil infiltration.
--G-(63 ×) Right frontal lobe cortical section, taken 6 hours following experimental TBI in animals treated with METH. Intraparenchymal vessel (★) with small contraction artifact halo. Pyknotic neuron (>) and only isolated intraparenchymal neutrophil (→)--.

TABLE 3-continued

Photomicrographs A-I of FIG. 5

H-(160 ×) Right frontal lobe cortical section, taken 6 hours following experimental TBI in animals treated with METH. Numerous pyknotic neurons with very few intraparenchymal neutrophils.
I-(63 ×) Right frontal lobe cortical section from sham control. Normal cellularity, no pyknotic cells, no intraparenchymal neutrophils.

I claim:

1. A method of treatment of a mammal, including humans, suffering from traumatic brain injury, which comprises administering to the sufferer a therapeutically effective amount of a compound of the formula

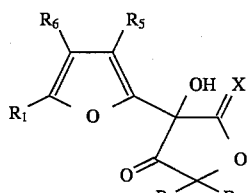 (I)

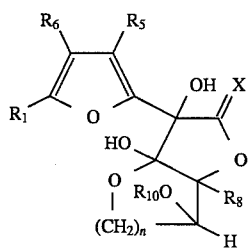 (II)

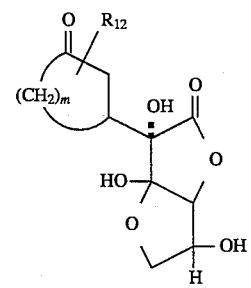 (III)

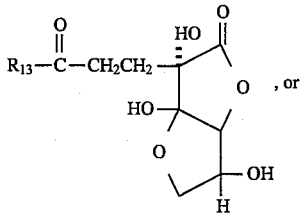 (IV)

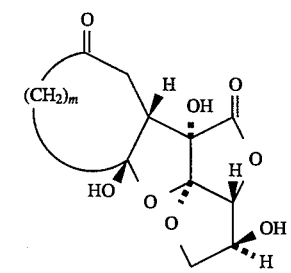 (V)

wherein:

$R_1$ is selected from the group consisting of hydrogen and lower alkyl;

$R_2$ is selected from the group consisting of hydrogen, lower alkyl and $CH_3YCH_2$—;

$R_5$ and $R_6$ are selected from the group consisting of hydrogen and lower alkyl and may be the same or different;

$R_8$ is selected from the group consisting of hydrogen and lower alkyl and may be the same or different;

$R_7$ may be $R_8$ or

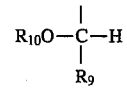

$R_9$ is selected from the group consisting of

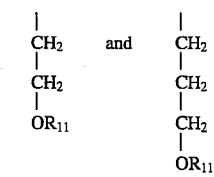

$R_{10}$ and $R_{11}$ are selected from the group consisting of hydrogen, lower alkyl, phenyl and hydroxyl substituted lower alkyl and may be the same or different;

when $R_7$ contains a hydroxyl group in the α, 62 or γ position, $R_7$ may form the hemiketal ring closure at carbon 3 of the butyrolactone with protonation of the carbonyl group on the same carbon atom;

$R_{12}$ is selected from the group consisting of hydrogen, lower alkyl and lower haloalkyl;

$R_{13}$ is lower alkyl;

m is 2, 3 or 4;

n is 1, 2 or 3;

X is O, S or NH; and

Y is O or S.

2. A method of treatment of an mammal, including humans, suffering from traumatic brain injury, which comprises administering to the sufferer a therapeutically effective amount of a compound of the formula

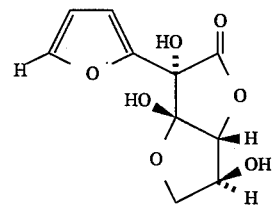 (IIA)

-continued (IIB)

(IIC)

(III)

wherein $R_{12}$ is lower alkyl, m is 2, 3 or 4, and $R_{13}$ is hydrogen, lower alkyl or lower haloalkyl.

3. A method according to claim 2, wherein the compound is

4. A method according to claim 2, wherein the compound is

5. A method according to claim 2, wherein the compound is

6. A method according to claim 2, wherein the compound is

7. A method according to claim 2, wherein the compound is

8. A method according to claim 2, wherein the compound is

9. A method according to claim 2, wherein the compound is

10. A method according to claim 2, wherein the compound is

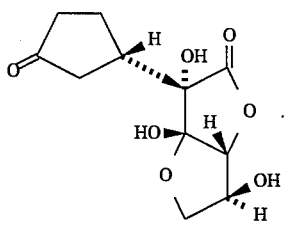

11. A method of treatment of a mammal, including humans, suffering from traumatic brain injury, which comprises administering to the sufferer a therapeutically effective amount of a compound of the formula

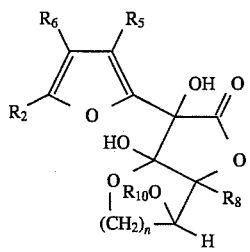

wherein:

$R_2$ is selected from the group consisting of hydrogen, lower alkyl and $CH_3YCH_2$—;

$R_5$ and $R_6$ are selected from the group consisting of hydrogen and lower alkyl and may be the same or different; $R_8$ is selected from the group consisting of hydrogen and lower alkyl and may be the same or different;

$R_{10}$ is selected from the group consisting of hydrogen, lower alkyl, phenyl and hydroxyl substituted lower alkyl and may be the same or different;

n is 1, 2 or 3;

X is O, S or NH; and

Y is O or S.

12. A method according to claim 11, wherein said compound is of the formula:

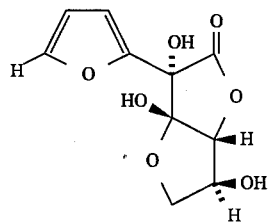

(IIA)

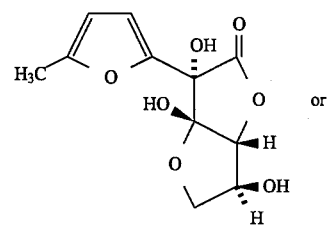

(IIB)

or

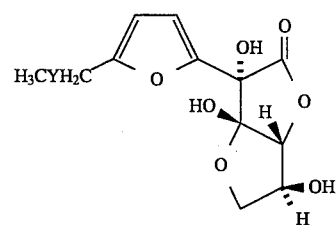

(IIC)

wherein Y is O or S.

* * * * *